US006733477B2

(12) United States Patent
Cowan et al.

(10) Patent No.: US 6,733,477 B2
(45) Date of Patent: May 11, 2004

(54) SYRINGES, SYRINGE TUBING AND FLUID TRANSFER SYSTEMS

(75) Inventors: Kevin P. Cowan, Allison Park, PA (US); Frederick W. Trombley, III, Gibsonia, PA (US); Mark Trocki, Cheswick, PA (US); David M. Reilly, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 238 days.

(21) Appl. No.: 09/731,108

(22) Filed: Dec. 6, 2000

(65) Prior Publication Data

US 2002/0068905 A1 Jun. 6, 2002

Related U.S. Application Data (60) Provisional application No. 60/169,413, filed on Dec. 7, 1999, provisional application No. 60/229,548, filed on Sep. 5, 2000, and provisional application No. 60/229,549, filed on Sep. 5, 2000.

(51) Int. Cl.[7] .................................................. A61M 5/00
(52) U.S. Cl. ...................................................... 604/181
(58) Field of Search ................................ 604/181, 182, 604/96.01, 54, 155; 210/195.2; 606/192

(56) References Cited

U.S. PATENT DOCUMENTS

| | | |
|---|---|---|
| 4,006,736 A | 2/1977 | Kranys et al. |
| 4,226,236 A | 10/1980 | Genese |
| 4,677,980 A | 7/1987 | Reilly et al. |
| 4,684,363 A * | 8/1987 | Ari et al. .................... 604/98 |
| 4,793,351 A * | 12/1988 | Landman et al. ............ 128/344 |
| 5,176,698 A * | 1/1993 | Burns et al. ................ 606/192 |
| 5,300,031 A | 4/1994 | Neer et al. |
| 5,356,375 A | 10/1994 | Higley |
| 5,383,858 A | 1/1995 | Reilly et al. |
| 5,439,452 A | 8/1995 | McCarty |
| 5,447,496 A * | 9/1995 | Bove et al. .................. 604/54 |
| 5,702,597 A * | 12/1997 | Chevallet et al. .......... 210/195.2 |
| 5,741,227 A | 4/1998 | Sealfon |
| 6,190,354 B1 * | 2/2001 | Sell et al. ................ 604/96.01 |
| 2001/0047153 A1 * | 11/2001 | Trocki et al. ................ 604/155 |

FOREIGN PATENT DOCUMENTS

| | | |
|---|---|---|
| DE | 196 01 214 | 8/1996 |
| DE | 196 33 530 | 2/1998 |
| EP | 0 736 306 | 10/1996 |
| WO | WO 96/32975 | 10/1996 |
| WO | WO 01/37903 | 5/2001 |

* cited by examiner

*Primary Examiner*—Henry Bennette
*Assistant Examiner*—Sabrina Dagostino
(74) *Attorney, Agent, or Firm*—Gregory L. Bradley (57) ABSTRACT

A syringe includes a body and a plunger disposed therein. The body includes a nozzle formed therein and at least one hub member connected thereto or integrally formed thereon for holding an end of a connector tube. The connector tube includes two ends, each end preferably being connected to a respective hub member to retain the connector tube in contact with the syringe. Preferably, the syringe and the connector tube are packaged in a pre-connected condition for ease of use by the customer. Furthermore, flexible inlet tubing for connection to a syringe for filling the syringe with contrast media, for example, is described. The inlet tubing permits filling of the syringe from either a bag or a bottle and may remain attached to the syringe so that it forms at least a part of the connection to the patient. In addition, an apparatus for facilitating the purge of air from a connector tube that will ultimately be connected between a syringe and a patient is described. The apparatus includes a purging tube connected to the distal end of the connector tubing from the syringe. The purging tube includes a venting cap at its distal end. A flow inhibitor is positioned under the venting cap to cooperate with the venting cap by discouraging the discharge of fluid from the distal end of the purging tube while permitting the discharge of air therefrom.

53 Claims, 10 Drawing Sheets

SYRINGES, SYRINGE TUBING AND FLUID TRANSFER SYSTEMS

CROSS-REFERENCE TO RELATED APPLICATIONS

This application claims priority to Provisional Application Serial No. 60/169,413, filed on Dec. 7, 1999, Provisional Application Serial No. 60/229,548, filed on Sep. 5, 2000, and Provisional Application No. 60/229,549, filed on Sep. 5, 2000, the contents of which are hereby incorporated by reference.

BACKGROUND OF THE INVENTION

The present invention relates generally to syringes for use with injectors and, more particularly, to syringes, syringe tubing and fluid transfer systems having features that improve the ease of use and efficiency of loading fluid in and ejecting fluid from the syringes.

A number of injector-actuated syringes and powered injectors for use in medical procedures such as angiography, computed tomography, ultrasound and MRI have been developed. For example, U.S. Pat. No. 4,006,736 discloses an apparatus for injecting fluid into the vascular system of a human being or an animal. Likewise, U.S. Pat. No. 4,677,980 discloses an angiographic injector and syringe wherein the drive member of the injector can be connected to, or disconnected from, the syringe plunger at any point along the travel path of the plunger via a releasable mechanism requiring rotation of the syringe plunger relative to the piston.

A front-loading syringe and injector system is disclosed in U.S. Pat. No. 5,383,858, the disclosure of which is hereby incorporated by reference. The syringes disclosed in U.S. Patent No. 5,383,858 can be securely front-loaded directly and accurately on the injector or on a pressure jacket attached to the injector, thereby facilitating the loading-unloading operation as compared to prior systems.

To load syringes with contrast fluid, a user typically connects a fill tube to the front nozzle or discharge outlet of the syringe and places the other end of the tube in a bottle or bag of contrast medium or other fluid. The plunger of the syringe is retracted (usually by means of the injector piston) to aspirate the contrast into the syringe until the desired amount is loaded into the syringe. After the syringe is filled, the fill tube is then typically discarded. Often, contrast or other fluid contained in the fill tube may drip therefrom onto the floor or the injector.

After the syringe is filled with fluid, a connector tube is connected to the discharge outlet of the syringe and the connecting tube is primed (typically by advancing the plunger in the syringe) to eject air from the syringe and the connector tube (i.e., to prevent air from being injected into the patient). While this technique is entirely effective in purging air from the tubing connected to the syringe, it is undesirable to have liquids dispensed from the end of the tube. Often, the liquids dispensed from the end of the tube foul the exterior surface of the tubing or fall onto the floor. When dealing with contrast media, this is particularly undesirable because the media is very sticky and has a tendency to migrate to whatever surface the operator touches after purging the tube.

When the patient is ready for the injection, the patient end of the connector tube is connected to, for example, a catheter, in a patient. During the time period between priming the connector tube and connecting the patient end of the connector tube to the patient, the patient end of the connector tube should be maintained in a sterile condition.

A significant amount of time and attention is required to properly load syringes with fluid and to connect and prime the connector tube. Consequently, it is very desirable to develop a new syringe or to improve existing syringes to reduce operator time and involvement in loading the syringe with fluid and/or in priming and connecting the connector tubing, while also minimizing or eliminating discharge of contrast medium or other fluid from the syringe or tubing associated with the syringe.

SUMMARY OF THE INVENTION

The present invention provides syringes, syringe tubing and a fluid transfer system that reduces the amount of time and vigilance necessary to load the syringe with fluid, such as contrast fluid, to connect the syringe to a patient and to prime the syringe and connector tube assembly. In addition, the present invention provides a purge tube that is designed to minimize leakage of contrast medium or other fluid therefrom. Further, the present invention provides a syringe and connector tube assembly operable to maintain the sterility of the connector tube for subsequent connection to a patient.

In a first aspect, a syringe includes a body and a plunger disposed therein. The body includes a nozzle formed therein and a latch connected thereto or integrally formed thereon for holding a second end of a fill tube. The first end of the fill tube is preferably pre-connected to the nozzle. A plastic or other sheath is removably disposed around the fill tube between the first and second ends to maintain the fill tube in a clean and/or sterile condition prior to use for filling/loading the syringe with contrast.

In addition, the diameter of the syringe nozzle may be enlarged to provide for increased volumetric fluid flow (and thereby faster fluid filling/loading) into the syringe. Preferably, the internal diameter of the syringe may be increased from 0.1 inches to approximately 0.2 to 0.25 inches. The enlarged syringe nozzle may also decrease the formation of air bubbles, which typically occurs during syringe filling, thereby resulting in less air needing to be expelled from the syringe and the connector tubing prior to injection and decreased risk of an inadvertent air injection into a patient.

In a preferred embodiment, the syringe is packaged with the first end of the fill tube pre-connected to the nozzle and the second end held in the latch. The sheath preferably covers the fill tube. After the syringe is removed from its packaging, the second end of the fill tube is removed from the latch and the sheath is removed from the fill tube and discarded. The second end of the fill tube is then placed in a contrast or other fluid container. The plunger of the syringe is retracted to fill the syringe with the fluid in the container. After a sufficient amount of the fluid is aspirated into the syringe, the fill tube may then be disconnected from the syringe and, preferably, discarded.

In a second aspect, a syringe includes a body and a plunger disposed therein. The body includes a nozzle formed therein and at least one hub member connected thereto or integrally formed thereon for holding an end of a connector tube. In a preferred embodiment, the at least one hub member comprises two hub members disposed on the syringe body. The connector tube includes two ends, each end being connected to a respective hub member to retain the connector tube in contact with the syringe. Preferably, the syringe and the connector tube are packaged in a pre-connected condition for ease of use by the customer.

After the syringe is filled with fluid and the fill tube is disconnected from the discharge outlet or nozzle of the syringe, one end of the connector tube is removed from a hub member and connected to the nozzle of the syringe. The second end of the connector tube is removed from the other hub member and held, preferably over a refuse or other container (i.e., to collect any fluid ejected from the connector tube during the priming operation), while the syringe and connector tube is primed to remove air therefrom. After the priming operation is completed, the second end of the connector tube is replaced on the hub member on the syringe to maintain it in a sterile condition and/or an "out of the way" location until the second or patient end of the connector tube is connected to the patient.

Further, the connector tube may include one or more tethered caps to prevent the caps from being dropped on the floor or misplaced. The caps are used to close the open ends of the connector tube to, for example, prevent dust or other contaminants from entering the connector tube. After the syringe is filled and/or primed, a cap may be placed on the open, patient end of the connector tube to maintain sterility. In a preferred embodiment, the caps are tethered to the connector tube by a plastic or other member connected between each of the caps and the connector tube.

In a third aspect, a fluid transfer system includes a syringe, a fluid container and a transfer device for transferring fluid, such as contrast, from the container to the syringe to fill same. In a preferred embodiment, the transfer device includes a spike for puncturing the seal of the fluid container, a container holder for holding the fluid container on the spike, a valve for allowing fluid to enter the syringe and a syringe support member for aligning the syringe nozzle with the valve.

After the syringe is mounted on an injector, the spike of the transfer device is used to pierce the seal of the fluid container. The syringe support member of the transfer device is then placed over the nozzle of the syringe. The luer tip of the syringe nozzle engages the valve of the transfer device, thereby allowing the contents of the fluid container to flow into the syringe. To aspirate the contents of the fluid container into the syringe, the piston of the injector retracts the plunger of the syringe.

The container holder functions to maintain the fluid container in contact with the spike and the fluid transfer device as the fluid is transferred from the fluid container to the syringe. In addition, the syringe support member maintains the nozzle of the syringe aligned and engaged with the valve, which is preferably a check valve. In a preferred embodiment, the transfer system is disposable.

In a fourth aspect, a syringe includes a body and a plunger disposed therein. The body includes a nozzle formed therein. Flexible inlet tubing may be pre-connected or permanently connected to the nozzle of the syringe (or provided separately) to facilitate filling of the syringe prior to a medical procedure. The flexible tubing may remain attached to the nozzle of the syringe after filling thereof to reduce waste and the opportunity for contrast or other fluid from dripping from the syringe nozzle or the inlet tubing.

In a fifth aspect, the present invention provides a purge tube that can be connected to the end of a connector tube that delivers contrast media or other fluid to a patient. The purge tube may minimize or eliminate the discharge of contrast media from the end of the connector tube that delivers the media to the patient when the syringe and connector tube assembly is purged. In a preferred embodiment, the purge tube may collect any discharged liquid from the end of the connector tube that delivers the contrast media to the patient. The purge tube may then be removed from the connector tube and discarded to minimize or eliminate contamination of other surfaces by the liquid captured thereby.

Other aspects of the invention and their attendant advantages will be discerned from the following detailed description when read in connection with the accompanying drawings.

BRIEF DESCRIPTION OF THE DRAWINGS

Various embodiments of the present invention will be described below, which reference to the following drawings, in which.

DETAILED DESCRIPTION OF THE INVENTION

Figure 1:
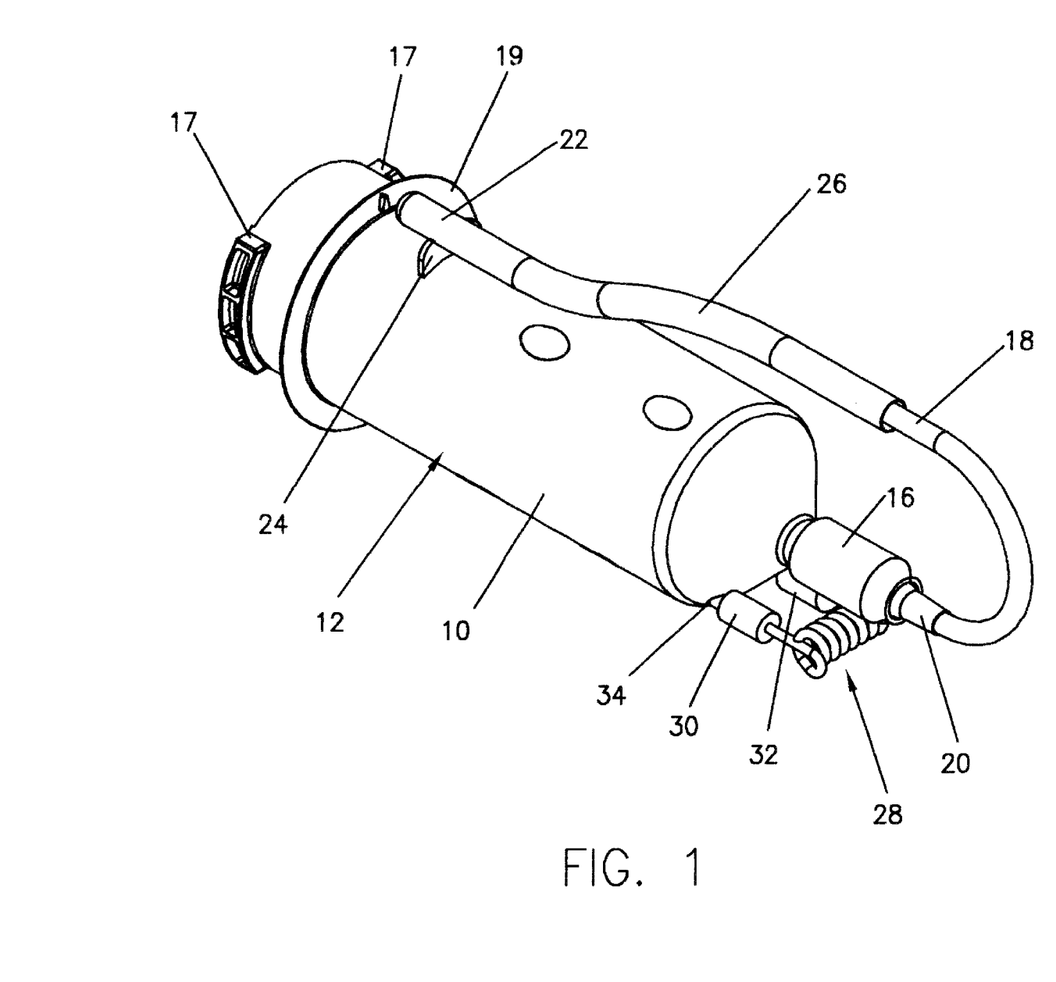
FIG. 1 is a perspective view of an embodiment of the syringe of the present invention in a first orientation.

As best shown in FIG. 1, a syringe 10 includes a body portion 12 and a plunger (not shown) movably disposed therein. The body portion 12 defines a nozzle or discharge outlet 16 at the front end thereof for discharging fluid contained within the syringe 10 to a patient and a latch or retention member 24 preferably disposed on a rearward end thereof.

The body portion 12 further includes at least two mounting flanges 17 and a sealing flange 19 for securely mounting the syringe on the front of an injector (not shown), as disclosed in U.S. Pat. No. 5,383,858, the contents of which are hereby incorporated by reference.

A fill tube 18 includes a first end 20 removably connected to the nozzle 16 of the syringe 10 and a second end 22 removably connected to the latch 24 on the body 12 of the syringe. A sheath 26, which may be formed of plastic or other suitable material, covers the fill tube 18 to maintain the fill tube in a clean or sterile condition.

The syringe 10 is preferably packaged in a container (not shown) with the first end 20 of the fill tube 18 pre-connected to the luer tip (not shown) of the nozzle 16 and the second end 22 pre-connected to the latch 24. In that manner, the operator does not have to connect the fill tube 18 to the syringe 10 before filling the syringe with fluid, which is convenient and saves operator time.

In use, after the syringe 10 is removed from its container, the second end 22 of the fill tube 18 is disconnected from the latch 24 and the sheath 26 is removed from the fill tube 18 (via the free second end 22). The second end 22 of the fill tube 18 may then be placed in a fluid container (not shown), such as a contrast container, to fill/load the syringe 10 with fluid. The fluid is aspirated into the syringe 10 by retracting the plunger within the syringe 10, preferably by means of the injector piston (not shown). After the syringe 10 is filled, the first end 20 of the fill tube 18 can be removed from the nozzle 16 of the syringe 10, and the fill tube 18 discarded.

Figure 2:
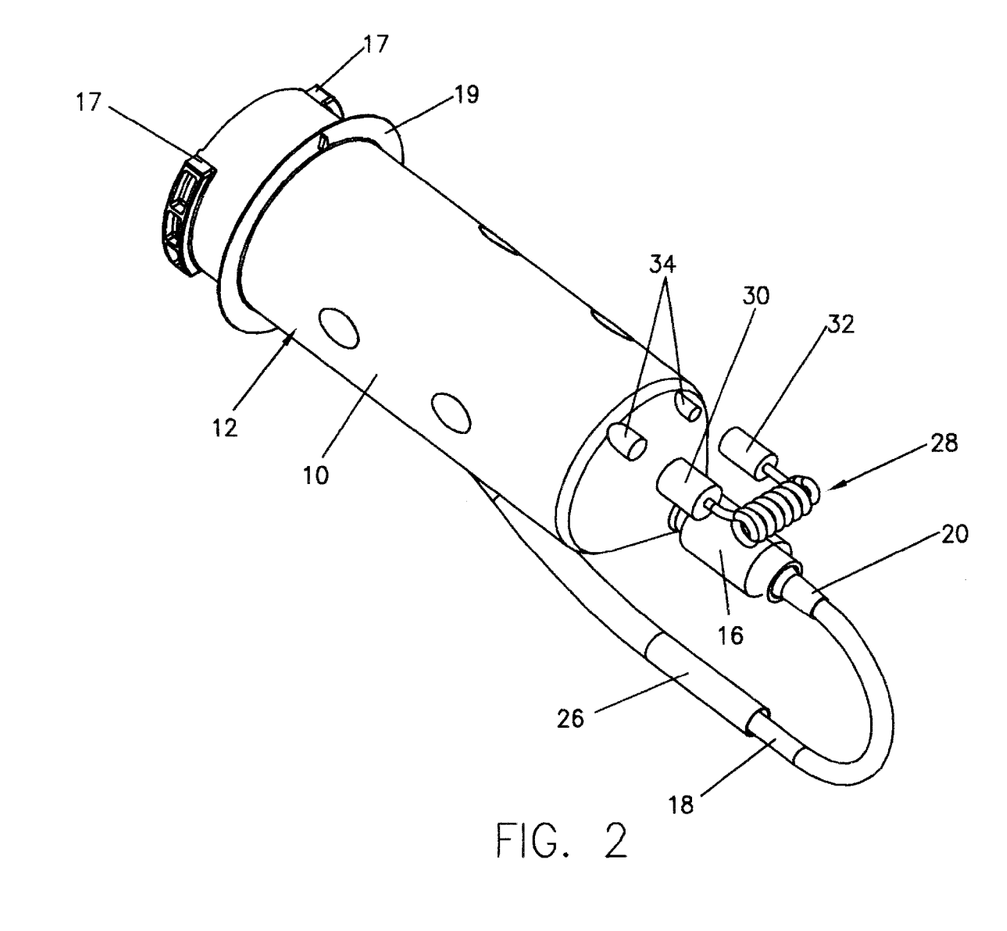
FIG. 2 is a partially exploded, perspective view of the syringe of FIG. 1 in a second orientation.
Figure 3:
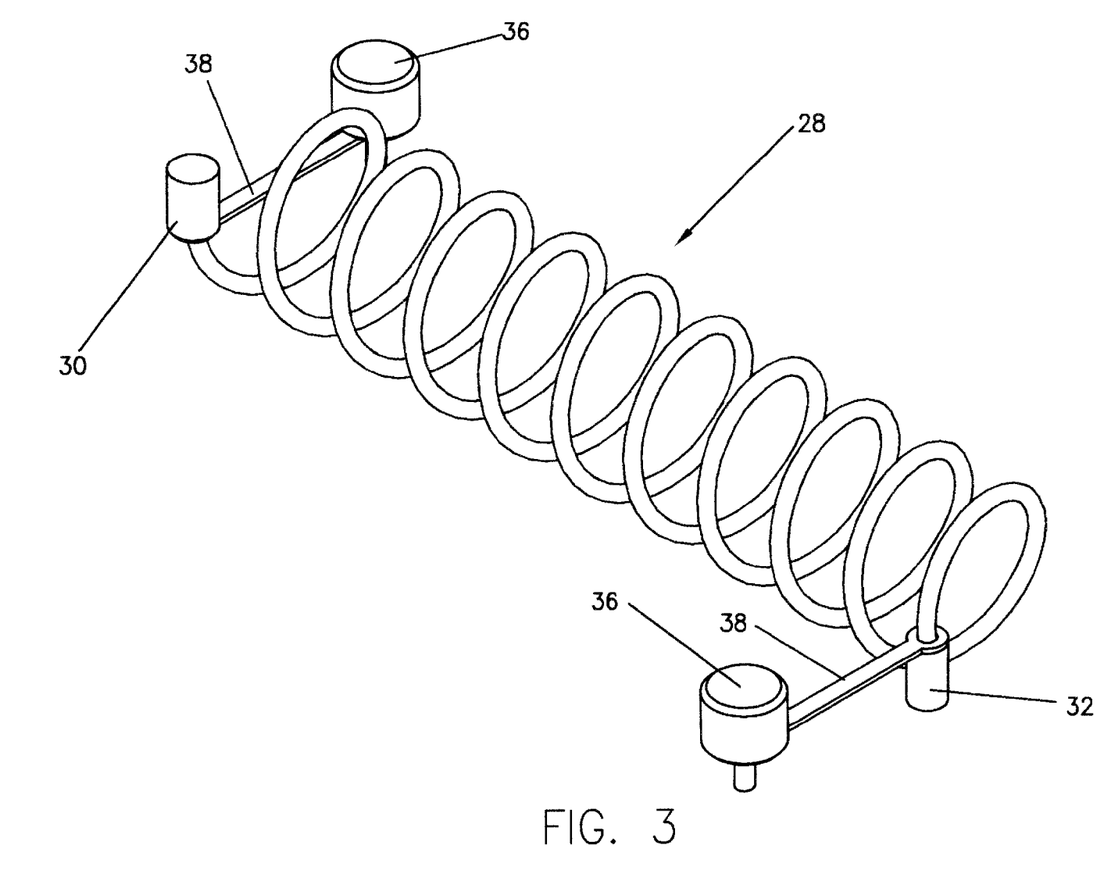
FIG. 3 is a perspective view of a connector tube with tethered caps for the ends thereof.

In addition, as best shown in FIGS. 2 and 3, a connector tube 28 may be pre-connected to the syringe 10. The connector tube 28 includes a first end 30 for connection to the nozzle 16 of the syringe 10 and a second or patient end 32 for connection to a patient (not shown). The syringe preferably includes two hub members 34 connected to or formed on the body portion 12 of the syringe. The ends 30, 32 of the connector tube 28 are removably connected to a respective hub member 34 on the syringe 10.

In use, the syringe 10 is preferably packaged with the ends 30, 32 of the connector tube 28 connected to the hub members 34 on the syringe 10. After the syringe is filled with fluid, the first end 30 of the connector tube 28 is connected to the nozzle 16 of the syringe 10. The syringe 10 and the connector tube 28 are then primed to remove air therefrom by advancing the plunger within the syringe 10. As a result, the air contained within the syringe 10, along with possibly a small amount of fluid, 10 is ejected from the syringe 10 and the second end 32 of the connector tube 28.

After the connector tube 28 is primed, the second end 32 of the tube 28 is reconnected to a hub member 34 until the operator is ready to connect the second end 32 to the patient. Alternately, the second end 32 may be connected to or draped over the latch 24 on the syringe 10. By mounting the second end 32 of the connector tube 28 on the hub member 34 or the latch 24, the second end 22 is kept clean and/or sterile and is placed in an "out of the way" location. Further, by effectively closing the open, second end 32 of the connector tube 28 with a hub member 34, fluid is prevented from leaking from the connector tube 28 onto the floor or elsewhere.

Moreover, after the injection procedure is completed, the second end 32 of the connector tube 28 may be removed from the patient and reconnected to a hub member 34 to prevent fluid spillage. After the syringe 10 is removed from the injector, the syringe 10 and connector tube 28 can be disposed of as a unit.

As shown in FIG. 3, the connector tube 28 may also include tethered caps 36 for each end 30, 32 thereof. The caps 36 may be used to close the open ends 30, 32 of the connector tube 28 to prevent dust and other contaminants from contaminating the connector tube 28 and to prevent fluid from leaking therefrom. For example, after the connector tube 28 has been attached to the syringe 10 and primed to remove air therefrom, a cap 36 may be placed over the open, patient end 32 of the connector tube 287 to maintain sterility prior to injection.

In a preferred embodiment, the caps 36 are tethered to the connector tube 28 by means of tethers 38 disposed between the connector tube 28 and the caps 36. The tethers 38 may be formed of plastic or any other suitable material.

Figure 4:
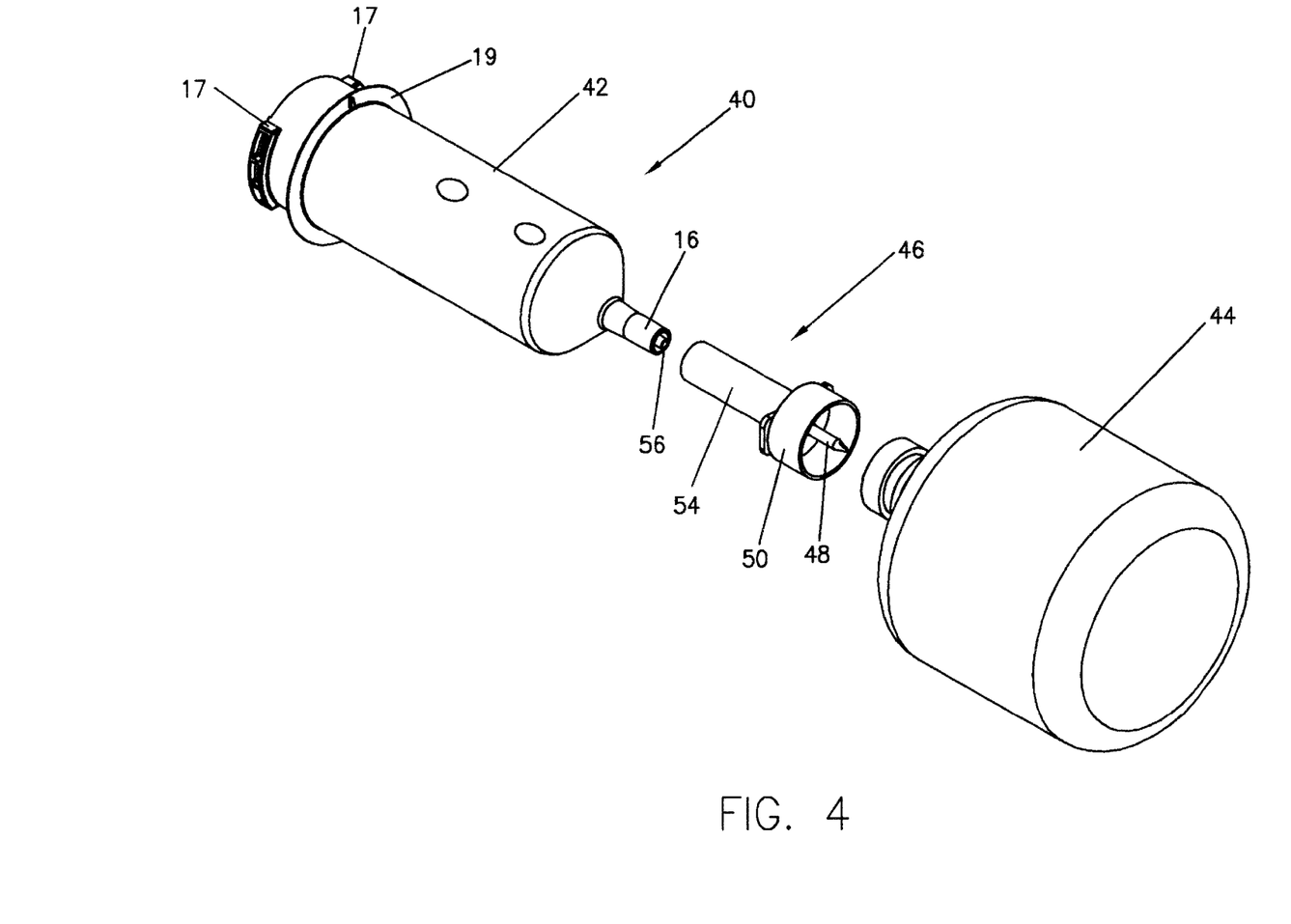
FIG. 4 is an exploded, perspective view of a preferred embodiment of the fluid transfer system of the present invention.

As shown in FIG. 4, a fluid transfer system 40 includes a syringe 42, a fluid container 44 and a transfer device 46 for transferring fluid, such as contrast, from the container 44 to the syringe 42 to fill it. (The syringe 42 may contain the same features as discussed above with respect to the syringe 10 shown in FIGS. 1 and 2.)

In a preferred embodiment, the transfer device 46 includes a conventional spike 48 for puncturing the seal of the fluid container 44, a container holder or cup 50 for holding the fluid container 44 on the spike 48, a valve (not shown), such as a check valve, for allowing fluid to enter the syringe 42 and a syringe support member or sleeve 54 for holding the syringe 42 in relationship to the transfer device 46.

After the syringe 42 is mounted on an injector (not shown), the plunger (not shown) is advanced to expel air from the syringe 42. The syringe 42 is then ready to be filled with fluid. The transfer device 46 may then be inserted onto the fluid container 44 such that the spike 48 pierces the seal of the fluid container 44. The syringe support member 54 of the transfer device 46 may then be placed over the nozzle of the syringe 42. Within the support member 54, the luer tip 56 of the syringe 42 engages and actuates the valve to open a passage for fluid to flow from the container 44 to the syringe 42. To aspirate the contents of the fluid container 44 into the syringe 42, the injector piston (not shown) retracts the plunger (not shown) of the syringe 42.

In a preferred embodiment, when the luer tip 56 of the syringe 42 opens the valve, fluid will not substantially flow from the container 44 until the plunger is retracted to create a suction to aspirate fluid into the syringe 42. This design prevents fluid from inadvertently spilling from the container 44. Further, the container holder 50 and the syringe support member 54 are designed to impart rigidity to the system and to maintain the syringe 42 and the container 44 in contact with the transfer device 46. In a preferred embodiment, the transfer system 46 is disposable.

Figure 5:
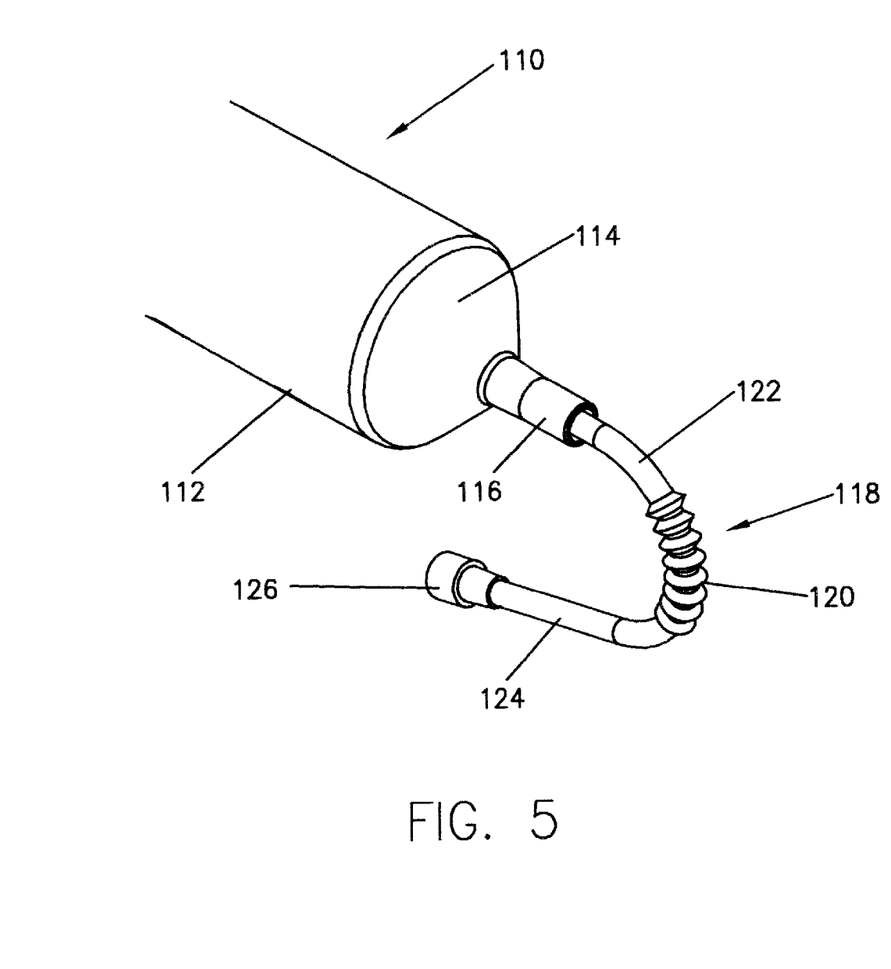
FIG. 5 is an isometric illustration of a syringe and flexible inlet tubing of the present invention.
Figure 6:
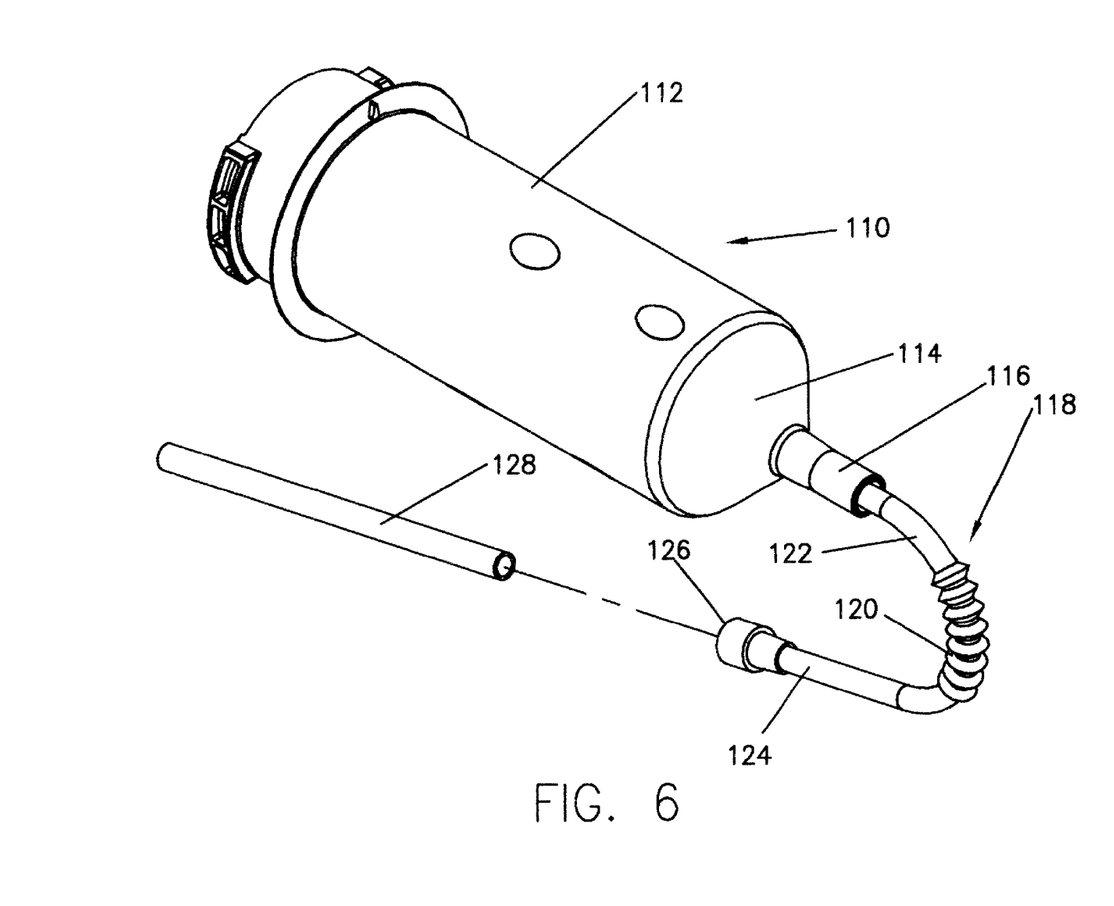
FIG. 6 is an isometric illustration of an alternate embodiment of the flexible tubing illustrated in FIG. 5.

A syringe and an inlet tube of the present invention are shown in FIGS. 5 and 6. The syringe 100 includes a cylindrical body 112 and a frusto-conical forward end 114 that transitions into a discharge end 116. A flexible inlet tube 118 is connected to the discharge end 116. Preferably, the flexible tube 118 contains a flexible (or corrugated) section 120 disposed between two smooth (or non-corrugated) sections 122, 124. Flexible tubing 118 may be composed of any suitable polymeric material so long as the material is flexible, durable, and suitable for medical use.

While flexible tubing 118 is illustrated with two smooth sections 122, 124 connected to one another by a corrugated section 120, other alternative constructions are contemplated within the scope of the present invention. For example, the flexible tube may include one corrugated section and one smooth (non-corrugated) section. In still another embodiment, the flexible tube may not include any corrugated sections at all, but instead, may incorporate some other alternative flexible section or sections to accomplish the same objective.

Flexible tubing 118 may be releasably connected to discharge or dispensing end 116 of syringe 110 or it may be permanently attached thereto. Similarly, flexible tubing 118 may be supplied with syringe 110 or it may be supplied separately and used with syringe 110. As can be readily appreciated, the flexible nature of inlet tube 118 allows it to be easily maneuvered for use with fluid bags or bottles to fill the syringe 110.

At the end of flexible tubing 118 opposite to the end connected to dispensing end 116 of syringe 110, a luer lock 126 is provided. After filling syringe 110, once filler bag or bottle has been removed from flexible tubing 118, a low-pressure connector tubing ("LPCT") may be connected directly to luer lock 126 for connection to the patient.

FIG. 6 illustrates another embodiment of the present invention, which is specifically directed at the filling of syringe 110 from a bottle of contrast medium. A tube extension 128 is illustrated that releasably connects to luer lock 126. The extension tubing 128 is inserted into the bottle of contrast media for filling syringe 110. After syringe 110 is filled, extension tubing 128 is removed from the bottle, disconnected from luer lock 126, and discarded. After purging, syringe 110 may then be connected to the patient.

The embodiment shown in FIG. 6 facilitates filling of syringe 110. In addition, tubing extension 128, which is usually covered with contrast media after syringe 110 is filled, may be discarded to reduce contamination of equipment with contrast media that may remain thereon.

Figure 7:
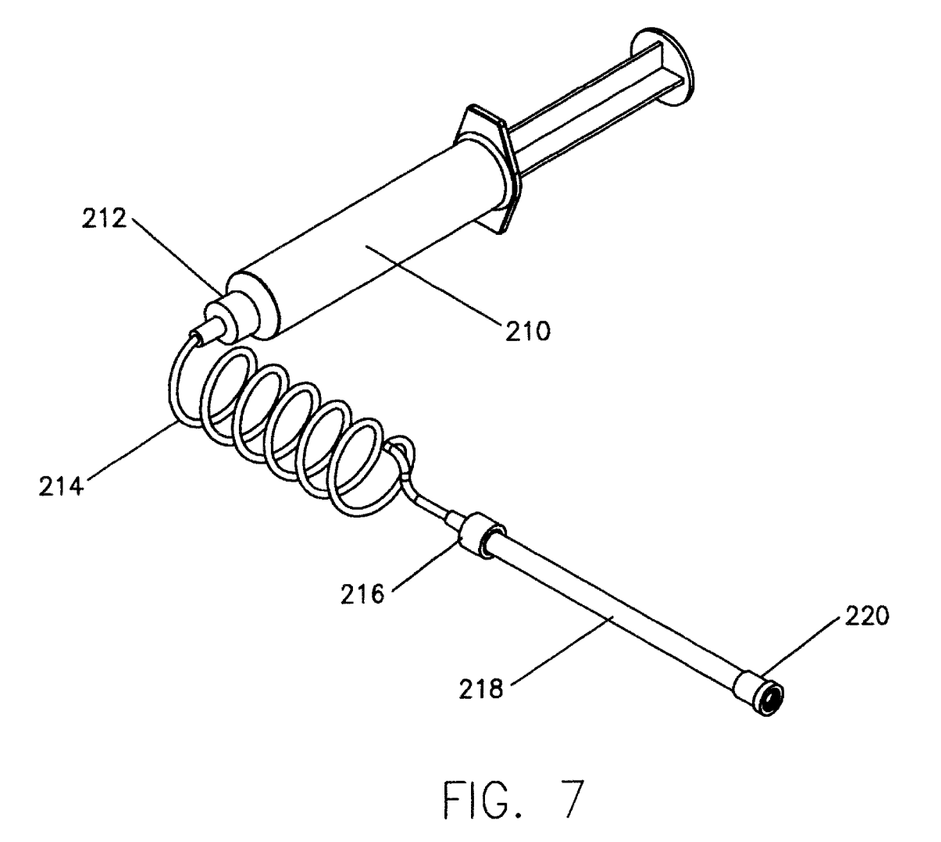
FIG. 7 is an isometric view of a purging tube of the present invention shown connected to a syringe.

A syringe and purging tube of the present invention is shown in FIGS. 7–10. FIG. 7 illustrates a syringe 210 with a discharge end 212. Discharge end 212 is usually provided with a luer lock so that a tube 214, such as a low-pressure connector tubing (or "LPCT"), may be connected thereto.

Figure 8:
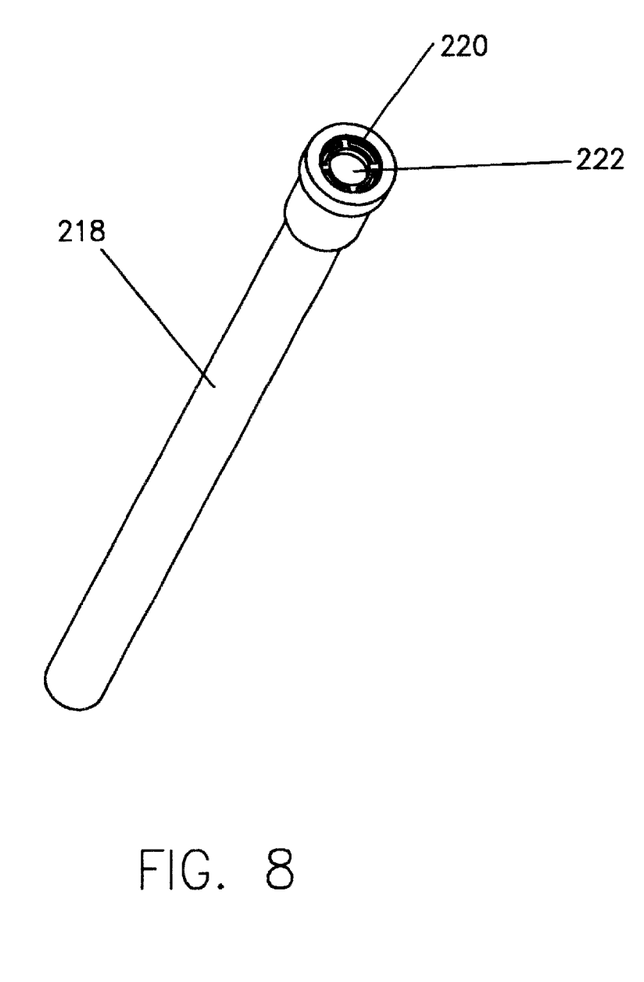
FIG. 8 is an enlarged view of the purging tube shown in FIG. 7.
Figure 9:
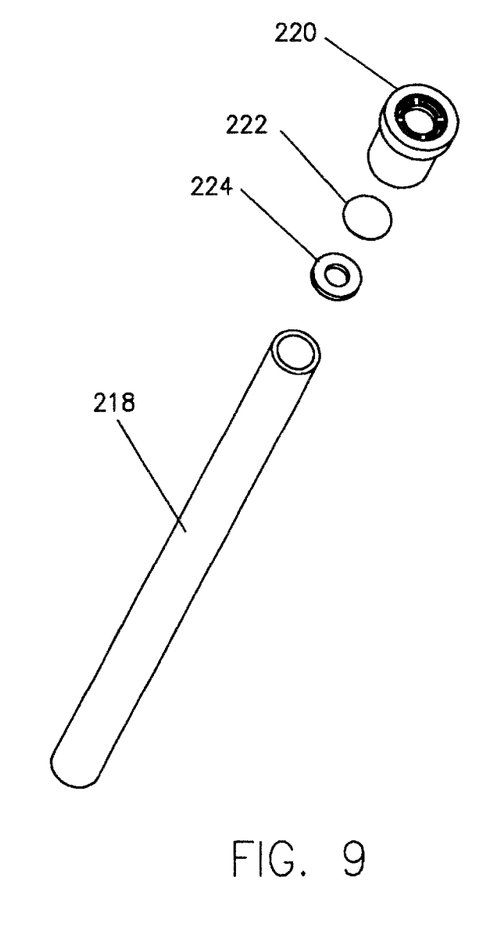
FIG. 9 is an isometric, exploded view of the purging tube shown in FIGS. 7 and 8.

In the embodiment illustrated, connector tube 124 includes a luer lock 216 at a distal end. A purging tube 218 is removably connected to the luer lock 216 of the connector tube 214. Purging tube 218, which is shown in detail in FIG. 8, has a vented cap 220 at the distal end thereof. As illustrated in FIG. 9, between purging tube 218 and vented cap 220 are disposed two additional elements, a flow preventor 222 and a seal (or spacer) 224. Seal 224 is disposed between purging tube 218 and flow preventor 222. Flow preventor 222 may be any suitable material (including paper) that inhibits the flow of contrast media, but allows air to pass therethrough and out of the end of purging tube 218. The vented cap 220, in a preferred embodiment, provides a support structure for the flow preventor 222 and allows air to pass therethrough from the flow preventor 222 to the atmosphere. In the preferred embodiment, flow preventor 222 is made of Goretex®, which is the trade name of a vapor-breathable fabric made by W. L. Gore and Associates.

After a syringe 210 is filled with a fluid, such as a contrast media, the air remaining in the LPCT 214 and the syringe 210 should be purged (e.g., by advancing the syringe plunger) before the LPCT 214 is connected to a patient. During purging, some contrast media will often be forced out of the distal end of the LPCT 214. Purging tube 218 is provided with a sufficiently large interior volume to collect that discharged media. In a preferred embodiment, the purging tube 218 is adapted to contain approximately 3 ml of fluid. In addition, the purge tube 218 is preferably pre-connected to the distal end of the LPCT 214. The vented cap 220 allows air to be discharged from the purge tube 218 and the flow preventor 222 inhibits leakage of contrast media from the distal end of purging tube 218 during the purging operation. As can be appreciated, while flow preventor 22 does inhibit the flow of fluid therethrough, it will not prevent fluid flow if a sufficient volume of fluid is discharged into the purge tube 218. Therefore, during the purging operation, an operator should be careful not to discharge into the purge tube 218 more fluid than the fluid volume capacity of the purge tube 218.

During the purging operation, the distal end of the purge tube 218 is preferably held in an elevated position (i.e., opposite from the ground) to further prevent fluid from being discharged from the purge tube 218. However, the purging operation could be conducted with the distal end of the purge tube 218 held in any orientation. After the purging operation is completed, the purge tube 218 contains the fluid discharged from the syringe 210 and the connector tubing 214. To prevent the discharged fluid from leaking out of the proximal end of the purge tube 218 (i.e., the end connected to the distal end of the LPCT 214), the proximal end of the purge tube 218 is preferably elevated prior to or immediately after being disconnected from the connector tube 214. Thereafter, the purge tube 218 is preferably discarded and the connector tube 214 is connected to a catheter in a patient for an injection procedure.

Purging tube 218 offers at least one further advantage. With purging tube 218, it is possible to design an injector that has an automatic purge feature. See, for example, the auto prime feature described in PCT International Application No. PCT/US00/31991, filed on Nov. 21, 2000, the contents of which are hereby incorporated by reference. Specifically, the injector (not shown) may have a button that the practitioner may push to clear air from syringe 210 and the LPCT 214. Upon actuation of the auto purge feature, the injector would advance the plunger in the syringe by a predetermined amount. By providing purging tube 218 with a sufficient interior volume, the auto purge feature should not exceed the interior volume of the purging tube 218.

Figure 10:
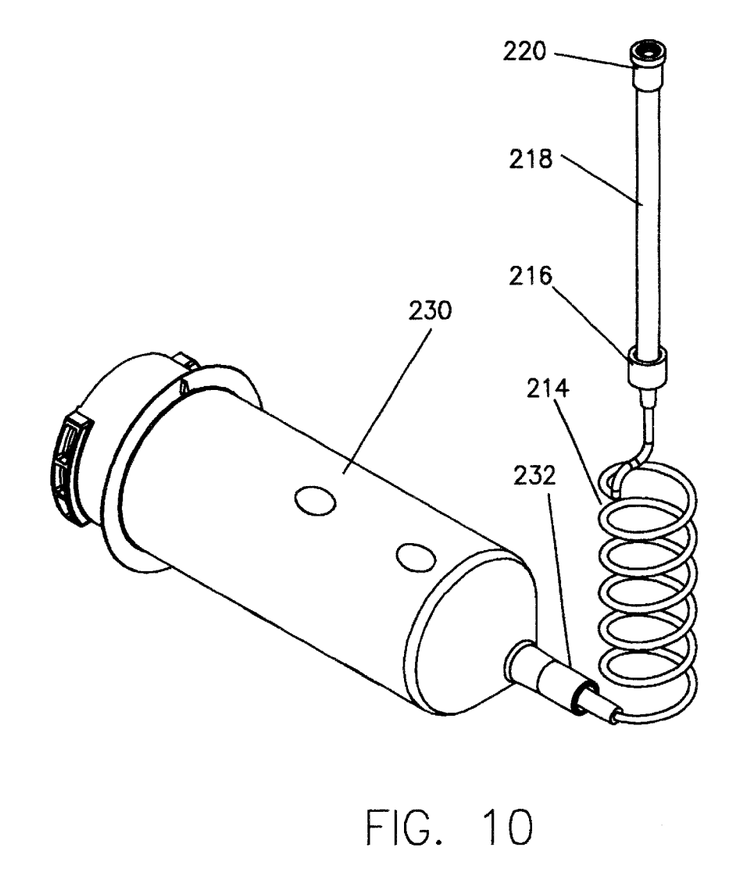
FIG. 10 is an isometric view of a syringe and the purging tube of the present invention.

FIG. 10 illustrates the purging tube 218 of the present invention in use with a syringe 230 having a discharge end 232. Syringe 230 may be of the type typically used for the injection of contrast media into a patient for vascular imaging, for example. While syringe 230 differs from syringe 210 shown in FIG. 7, in all other respects the use and function of purging tube 218 is the same as described above.

In an alternate embodiment, the vented cap 220 and the flow preventor 222 may be positioned at a location between the proximal and distal ends of the purge tube 218. When fluid is discharged into the purge tube 218 past the vented cap 220 and the flow preventor 222 (i.e., to the distal side thereof) during the purging operation, the fluid will cooperate with the flow preventor 222 to prevent the fluid from leaking from the proximal and distal ends of the purge tube 218 after the purge tube 218 is disconnected from the connector tube 214. This alternate design may reduce the need for the operator to elevate the proximal end of the purge tube 218 prior to or immediately after it is disconnected from the connector tube 218, as discussed above with respect to the preferred embodiment.

In yet another embodiment, the vented cap 220 and flow preventor 222 may be replaced with a one-way check valve (not shown) that is biased in a closed position. During the purging operation, the check valve would be forced open to allow air to pass therethrough. After the purging operation is completed, the check valve will close and, when the purge tube 218 is disconnected from the LPCT 214, operate to prevent fluid from leaking from the proximal and distal ends of the purge tube 218.

Furthermore, while one aspect of the present invention has been described above in terms of a purging "tube," it should be appreciated that the term "tube" is not limiting and should be construed to include all suitable types of structures and containers for retaining the discharged fluid from the syringe and the LPCT 214.

Although the present invention has been described in detail in connection with the above examples and embodiments, it is to be understood that such detail is solely for that purpose and that those skilled in the art can make variations without departing from the invention. The invention is not limited to the disclosed embodiments, but may be practiced within the full scope of the appended claims.

What is claimed is:

1. A syringe assembly comprising:
   a syringe body defining a discharge end;
   a plunger movably disposed within the syringe body;

a connector tube comprising a distal end and a first end connected to the discharge end of the syringe body; and a purge tube defining a distal end and a proximal end, the proximal end of the purge tube adapted to be connected to the distal end of the connector tube for collecting fluid expelled from the syringe body and the connector tube during a purging operation, the purge tube comprising:

a vent member disposed between the distal end and the proximal end of the purge tube, the vent member being adapted to substantially permit air to pass therethrough; and a flow preventor operably associated with the vent member, the flow preventor being operable to substantially prevent egress of collected fluid from the purge tube and to substantially permit air to pass therethrough and out of the purge tube through the vent member.

2. The syringe assembly of claim 1 wherein the vent cap is disposed at the distal end of the purge tube, and the flow preventor is disposed between the vent cap and the purge tube.

3. The syringe assembly of claim 1 wherein the distal end of the connector tube comprises a luer connector.

4. The syringe assembly of claim 1 wherein the distal end of the connector tube is connectable to a patient catheter.

5. The syringe assembly of claim 1 wherein the purge tube is pre-connected to the connector tube.

6. The syringe assembly of claim 1 wherein fluid purged from the syringe is retained within the purge tube.

7. The syringe assembly of claim 6 wherein the purge tube is adapted to contain approximately 3 ml of fluid.

8. The syringe assembly of claim 1, further comprising a seal disposed between the purge tube and the flow preventor to further prevent the egress of fluid from the purge tube.

9. The syringe assembly of claim 1 wherein the purge tube further comprises a check valve.

10. A fluid transfer system comprising:

a syringe comprising a body portion and a plunger movably disposed therein, the body portion comprising a nozzle defining a luer tip;

a fluid container comprising a seal; and a transfer device comprising a piercing member and a valve in fluid communication with the piercing member, the luer tip operable to actuate the valve and the piercing member operable to pierce the seal of the fluid container to form a fluid passage between the fluid container and the syringe, whereby fluid is caused to flow from the container to the syringe as the plunger is retracted in the body portion of the syringe.

11. The syringe assembly of claim 2 further comprising a seal disposed between the distal end of the purge tube and the flow preventor to further prevent the egress of fluid from the purge tube.

12. The syringe assembly of claim 1 wherein the flow preventor comprises a vapor-breathable fabric.

13. The syringe assembly of claim 1 wherein the flow preventor comprises paper.

14. The syringe assembly of claim 1 wherein the syringe body comprises at least one mounting flange.

15. The syringe assembly of claim 14 wherein the at least one mounting flange comprises two mounting flanges.

16. The syringe assembly of claim 14 wherein the at least one mounting flange is located adjacent to a proximal end of the syringe body.

17. The syringe assembly of claim 14 further comprising a sealing flange located forward of the at least one mounting flange.

18. The fluid transfer system of claim 10 wherein the piercing member comprises a spike.

19. The fluid transfer system of claim 10 the valve comprises a check valve.

20. The fluid transfer system of claim 10 wherein the transfer device is disposable.

21. The fluid transfer system of claim 10 wherein the transfer device further comprises a container holder for supporting the fluid container on the piercing member.

22. The fluid transfer system of claim 10 wherein the transfer device further comprises a syringe support member for supporting the syringe in relation thereto.

23. The fluid transfer system of claim 10, further comprising:

a piston of an injector for engaging and retracting the plunger of the syringe to cause the fluid to flow from the container to the syringe.

24. The fluid transfer system of claim 10 wherein the transfer device further comprises a container holder for supporting the fluid container on the piercing member and a syringe support member for supporting the syringe in relation thereto.

25. The fluid transfer system of claim 24 wherein the container holder and the syringe support member are operable to impart rigidity to the fluid transfer system and to support the syringe and the fluid container in contact with the transfer device.

26. The fluid transfer system of claim 10 wherein the syringe body portion comprises at least one mounting flange.

27. The fluid transfer system of claim 26 wherein the at least one mounting flange comprises two mounting flanges.

28. The fluid transfer system of claim 26 wherein the at least one mounting flange is located adjacent to a proximal end of the syringe body portion.

29. The fluid transfer system of claim 26 further comprising a sealing flange located forward of the at least one mounting flange.

30. A syringe assembly comprising:

a syringe body defining a discharge end;

a plunger movably disposed within the syringe body;

a connector tube comprising a distal end and a first end connected to the discharge end of the syringe body;

a purge tube defining a distal end and a proximal end, the proximal end of the purge tube adapted to be connected to the distal end of the connector tube for collecting fluid expelled from the syringe body and the connector tube during a purging operation, the purge tube comprising:

a vent cap disposed at the distal end of the purge tube; and a flow preventor disposed between the vent cap and the purge tube, the flow preventor being operable to substantially prevent egress of collected fluid from the purge tube; and a seal disposed between the distal end of the purge tube and the flow preventor to further prevent the egress of fluid from the purge tube.

31. The syringe assembly of claim 30 wherein the distal end of the connector tube comprises a luer connector.

32. The syringe assembly of claim 30 wherein the distal end of the connector tube is connectable to a patient catheter.

33. The syringe assembly of claim 30 wherein the purge tube is pre-connected to the connector tube.

34. The syringe assembly of claim 30 wherein fluid purged from the syringe is retained within the purge tube.

35. The syringe assembly of claim 34 wherein the purge tube is adapted to contain approximately 3 ml of fluid.

36. The syringe assembly of claim 30 wherein the vent cap is adapted to allow air to escape from the purge tube.

37. The syringe assembly of claim 30 wherein the flow preventor comprises a vapor-breathable fabric.

38. The syringe assembly of claim 30 wherein the flow preventor comprises paper.

39. The syringe assembly of claim 30 wherein the syringe body comprises at least one mounting flange.

40. The syringe assembly of claim 39 wherein the at least one mounting flange comprises two mounting flanges.

41. The syringe assembly of claim 30 wherein the at least one mounting flange is located adjacent to a proximal end of the syringe body.

42. The syringe assembly of claim 30, further comprising a sealing flange located forward of the at least one mounting flange.

43. A syringe assembly comprising:

a syringe body defining a discharge end;

a plunger movably disposed within the syringe body;

a connector tube comprising a distal end and a first end connected to the discharge end of the syringe body; and a purge tube comprising a check valve and adapted to be connected to the distal end of the connector tube for collecting fluid expelled from the syringe body and the connector tube during a purging operation.

44. The syringe assembly of claim 43 wherein the check valve is a one-way check valve.

45. The syringe assembly of claim 43 wherein the distal end of the connector tube comprises a luer connector.

46. The syringe assembly of claim 43 wherein the distal end of the connector tube is connectable to a patient catheter.

47. The syringe assembly of claim 43 wherein the purge tube is pre-connected to the connector tube.

48. The syringe assembly of claim 43 wherein fluid purged from the syringe is retained within the purge tube.

49. The syringe assembly of claim 48 wherein the purge tube is adapted to contain approximately 3 ml of fluid.

50. The syringe assembly of claim 43 wherein the syringe body comprises a least one mounting flange.

51. The syringe assembly of claim 50 wherein the at least one mounting flange comprises two mounting flanges.

52. The syringe assembly of claim 43 wherein the at least one mounting flange is located adjacent to a proximal end of the syringe body.

53. The syringe assembly of claim 43, further comprising a sealing flange located forward of the at least one mounting flange.

* * * * *

UNITED STATES PATENT AND TRADEMARK OFFICE
CERTIFICATE OF CORRECTION

PATENT NO.      : 6,733,477, B2
APPLICATION NO. : 09/731108
DATED           : May 11, 2004
INVENTOR(S)     : Cowan et al.

Page 1 of 1

It is certified that error appears in the above-identified patent and that said Letters Patent is hereby corrected as shown below:

On the Title Page,

Item [75] - Inventors:
        Replace with:

--Kevin P. Cowan, Allison Park, PA (US); Frederick W. Trombley, III, Gibsonia, PA (US)--

Signed and Sealed this

Fourth Day of March, 2008

JON W. DUDAS
*Director of the United States Patent and Trademark Office*